(12) United States Patent
Primavera

(10) Patent No.: US 9,119,317 B2
(45) Date of Patent: Aug. 25, 2015

(54) METHOD OF FOLDING FLEXIBLE SUBSTRATE IN-SITU USING FOLD-ASSISTING FRAME

(71) Applicant: BIOTRONIK SE & Co. KG, Berlin (DE)

(72) Inventor: Anthony A. Primavera, Newberg, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 14/097,984

(22) Filed: Dec. 5, 2013

(65) Prior Publication Data

US 2014/0090243 A1 Apr. 3, 2014

Related U.S. Application Data

(62) Division of application No. 13/278,692, filed on Oct. 21, 2011, now abandoned.

(60) Provisional application No. 61/424,691, filed on Dec. 20, 2010.

(51) Int. Cl.
*A61N 1/375* (2006.01)
*H05K 1/02* (2006.01)
*H05K 7/16* (2006.01)

(52) U.S. Cl.
CPC .............. *H05K 7/16* (2013.01); *A61N 1/3758* (2013.01); *H05K 1/028* (2013.01); *H05K 2203/0169* (2013.01); *Y10T 29/49002* (2015.01); *Y10T 29/49117* (2015.01); *Y10T 29/5327* (2015.01)

(58) Field of Classification Search
CPC . A61B 1/041; H05K 1/189; H05K 2201/057; H05K 2201/2009; H05K 2201/2018; H05K 2201/2027; H05K 1/028; H05K 2203/0169; H05K 7/1435; H05K 7/16; A61N 1/3758; Y10T 29/49002
USPC .......................................................... 29/729
See application file for complete search history.

(56) References Cited

U.S. PATENT DOCUMENTS 5,170,326 A 12/1992 Meny et al.
5,371,569 A 12/1994 Tanaka
(Continued)

FOREIGN PATENT DOCUMENTS

SU 712987 1/1980
SU 712987 A * 1/1980

OTHER PUBLICATIONS

Lim, Shereen, "Recommendations for Installing Flash LEDs on Flex Circuits", White Paper, Avago Technologies, Mar. 19, 2010.
(Continued)

*Primary Examiner* — Livius R Cazan
(74) *Attorney, Agent, or Firm* — Buchanan Ingersoll & Rooney PC

(57) ABSTRACT

A method for manufacturing devices built on flexible substrates employs an in-situ, fold-assisting device frame. The fold-assisting frame conforms to a portion of the interior volume within the package, such that one or more pivoting members of the frame may be used as an in-situ, bending jig, in place of conventional bending equipment, to support and fold the planar flexible substrate into a desired three-dimensional configuration. The frame may accommodate placement of an unfolded or partially folded flexible circuit board so that a fold-assisting feature, such as a hinge, incorporated into the frame attaches to the flexible circuit board and closes around a pivot point to gently bend the circuit board into place, thus creating a three-dimensional folded circuit. Such a fixture and method facilitate packaging electronic devices in a compact form, with application to a wide range of mobile consumer electronics, including, for example, implantable medical devices.

7 Claims, 8 Drawing Sheets

(56) References Cited

U.S. PATENT DOCUMENTS

| | | |
|---|---|---|
| 5,434,362 A | 7/1995 | Klosowiak et al. |
| 5,717,556 A | 2/1998 | Yanagida |
| 5,814,090 A | 9/1998 | Latterell et al. |
| 5,998,738 A * | 12/1999 | Li et al. .................. 174/250 |
| 6,061,243 A | 5/2000 | Barnett et al. |
| 6,245,092 B1 | 6/2001 | Schaldach, Jr. |
| 7,337,003 B2 | 2/2008 | Malinowski |
| 7,656,673 B1 | 2/2010 | Fries et al. |
| 2010/0076533 A1 | 3/2010 | Dar et al. |

OTHER PUBLICATIONS

European Search Report and Annex to the European Search Report on European Patent Application No. EP 11 19 3759, dated Apr. 3, 2012 (6 pages).

* cited by examiner

METHOD OF FOLDING FLEXIBLE SUBSTRATE IN-SITU USING FOLD-ASSISTING FRAME

RELATED APPLICATION

This patent application is a divisional application claiming priority to U.S. patent application Ser. No. 13/278,692, filed Oct. 21, 2011, now abandoned, which claims priority to U.S. Provisional Application No. 61/424,691, filed on Dec. 20, 2010, the disclosures of which are hereby incorporated by reference in their entirety.

TECHNICAL FIELD

The present disclosure concerns methods of folding or bending flexible substrates and, in particular, concerns methods for manufacturing electronic devices that entail folding flexible circuit boards.

BACKGROUND

Flexible circuit boards are commonly used in compact mobile electronic and telecommunications devices including, but not limited to, cell phones, cameras, handheld computers, MP3 players, global positioning system (GPS) mapping devices, implantable medical devices, and the like, in which efficient use of space inside a device package, or housing, is a feature of critical importance. A typical sequence of steps for manufacturing such mobile devices includes populating a planar flexible substrate with electronic components by mounting components on both sides of the substrate, folding the planar circuit into a desired three-dimensional configuration, and then placing the three-dimensional folded circuit inside the device package, which may be outfitted with a supporting device frame. The planar flexible substrate may be formed into a regular or an irregular shape, and it may include tabs or extensions that, when folded, conform to the interior shape of the housing or that accommodate other parts contained within the housing, such as, for example, batteries, telemetry units, and digital memory chips. Flexible substrates are often made of polyimide or a similar type of polymer that may comprise a multi-layer laminate.

A circuit folding assembly operation typically involves the use of a complex, customized fixture, such as, for example, a specialized jig for holding and supporting the flexible substrate during a mechanized bending process, so as to avoid creasing the substrate, rupturing interconnecting wires, subjecting the substrate or components mounted thereon to high stresses during folding, or otherwise damaging the substrate and/or components. An exemplary multi-step bending process that relies on such equipment is described in a published white paper by Shereen Lim from Avago Technologies, entitled "*Recommendations for Installing Flash LEDs on Flex Circuits*". Often, adhesive or mechanical fixation is required to maintain the final, folded, three-dimensional configuration. Customized supporting accessories such as, for example, rigidizer plates, pallets, mandrels, clamps, and the like, are also commonly used to assist in the bending process, as described in U.S. Pat. No. 5,434,362 to Klosowiak, et al., entitled "Flexible Circuit Board Assembly and Method". Such tools increase manufacturing costs and complexity, because a new jig and accompanying accessories must be designed and constructed for each new folded circuit configuration. Often, operator intervention is also necessary during folding, which may include a series of multiple bends and/or multiple manual fixation steps. After the bending process is complete, the folded circuit must be aligned with the supporting frame, manually held in place so as not to disturb the folded shape, and then carefully inserted into the housing.

The presently disclosed invention is directed toward overcoming one or more of the above-identified problems.

SUMMARY

Instead of folding a planar flexible substrate prior to placing it inside a package, a novel, preferred method of manufacturing devices built on flexible substrates employs an in-situ, fold-assisting device frame. The fold-assisting frame generally conforms to the shape of a portion of the interior volume within the package, such that one or more pivoting members of the frame itself may be used as an in-situ bending jig, in place of conventional bending equipment, to support and fold the planar flexible substrate into a desired three-dimensional configuration. In an exemplary embodiment, the fold-assisting frame may accommodate placement of an unfolded or partially folded flexible circuit board, so that a hinge or other pivot feature incorporated into the frame attaches to the flexible circuit board and closes around a pivot point to gently bend the circuit board into place, thus creating a three-dimensional folded circuit.

A method of folding a planar flexible substrate, in-situ, within a device frame includes providing a flexible frame of which at least a portion conforms to an interior shape of a package, aligning a pivoting portion of the frame with a corresponding portion of the flexible substrate, securing the flexible substrate portion to the pivoting portion, bending the two together so as to achieve a desired three dimensional configuration that fits conformally within the package, and optionally latching the pivoting portion of the flexible frame and the substrate portion in their final positions to maintain the desired three-dimensional configuration. Such a fixture and method facilitate packaging electronic devices in a compact form, with application to a wide range of mobile consumer electronics, including, but not limited to, implantable medical devices.

Various other objects, aspects and advantages of the presently disclosed invention can be obtained from a study of the specification, the drawings, and the appended claims.

DETAILED DESCRIPTION

Figure 1:
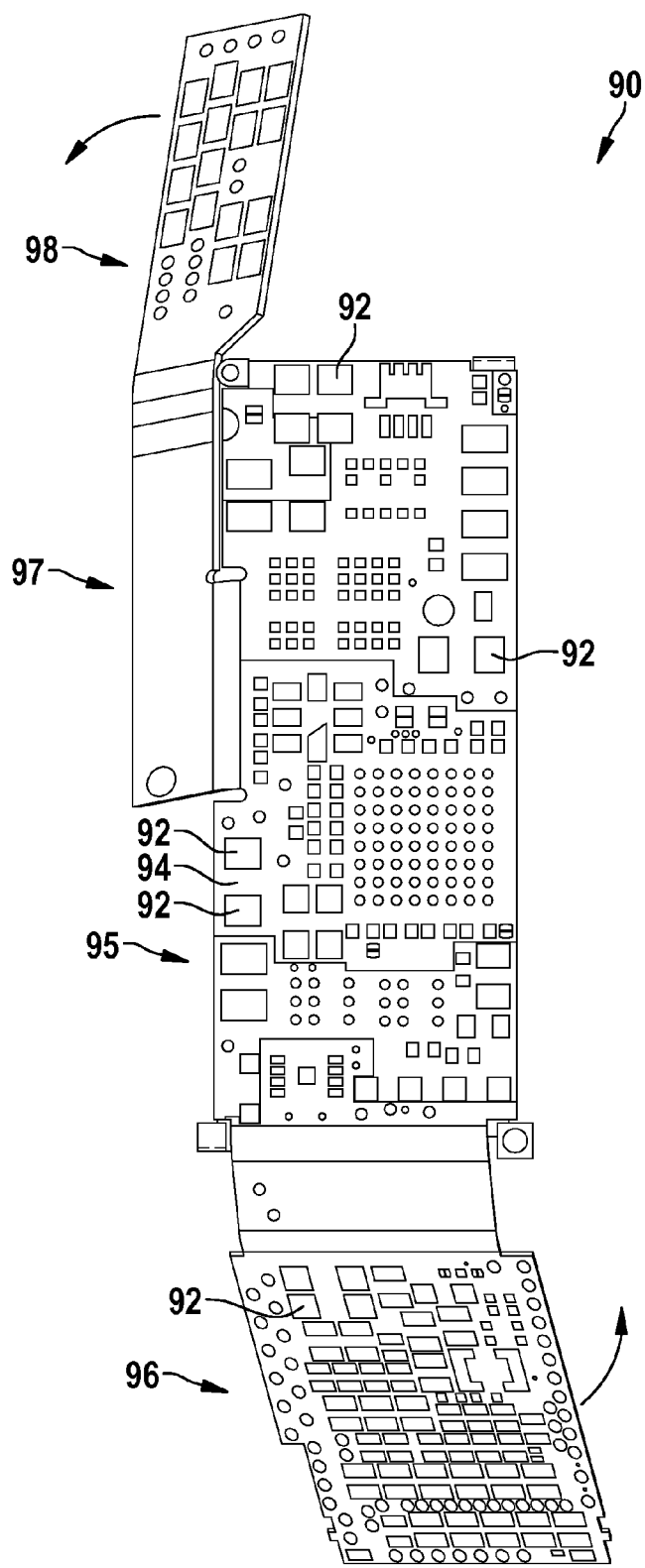
FIG. 1 illustrates a prior art foldable circuit for use in a compact mobile electronic device.

Embodiments of the present invention will be readily understood from the following detailed description in conjunction with the accompanying drawings. To facilitate this description, like reference numerals designate like structural elements. Embodiments of the invention are illustrated by way of example, and not by way of limitation, in the figures of the accompanying drawings.

An example of a conventional foldable "flex" circuit 90 for use, e.g., in an implantable cardiac device is shown in FIG. 1. In this example, the foldable flex circuit 90 generally consists of electronic type device components 92 mounted on a flexible substrate 94. In the example shown, foldable circuit 90 has four sections: a fixed upper section 95; a lower section 96 designed to bend 180-degrees as shown into a plane parallel to, and behind, the fixed upper section 95; a lower extension 97 designed to bend away, perpendicular to the plane of the fixed upper section 95; and an upper extension 98 that is designed to rotate counter-clockwise.

Figure 2:
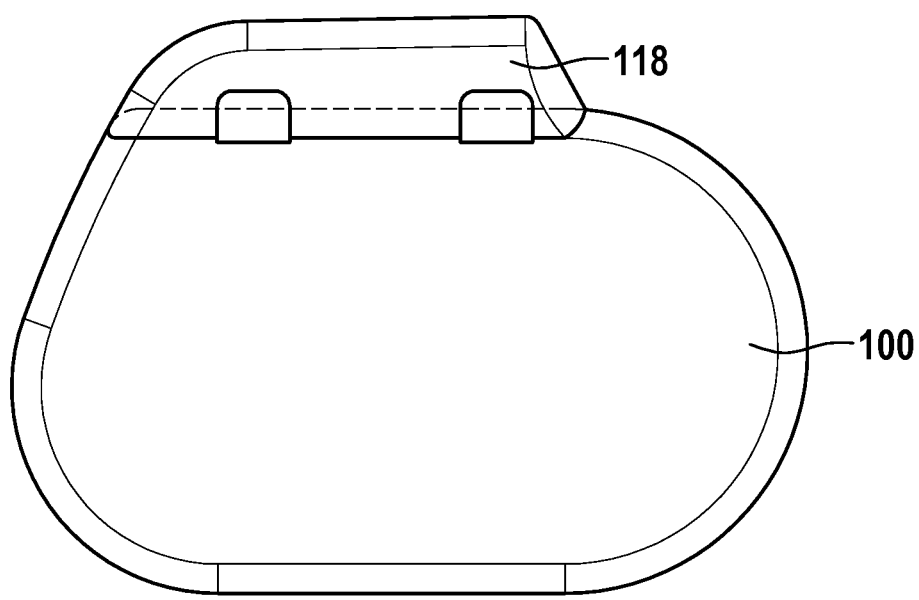
FIG. 2 is a pictorial plan view of a prior art mobile electronic device housing for an implantable medical device (IMD), which contains the foldable circuit shown in FIG. 1.
Figure 3:
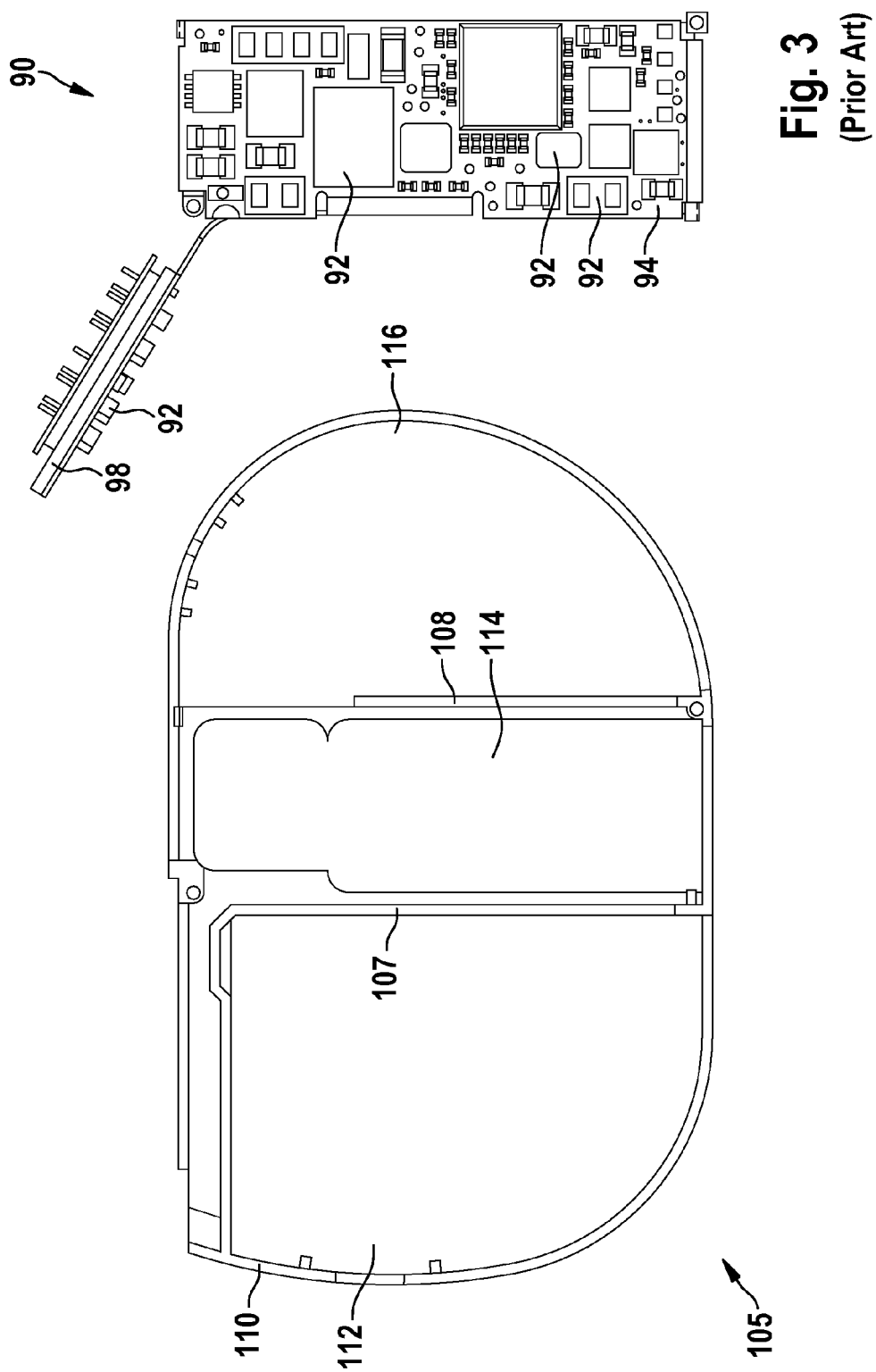
FIG. 3 is a side elevation view of a prior art device frame and a flexible circuit board having a pre-folded extension.
Figure 4:
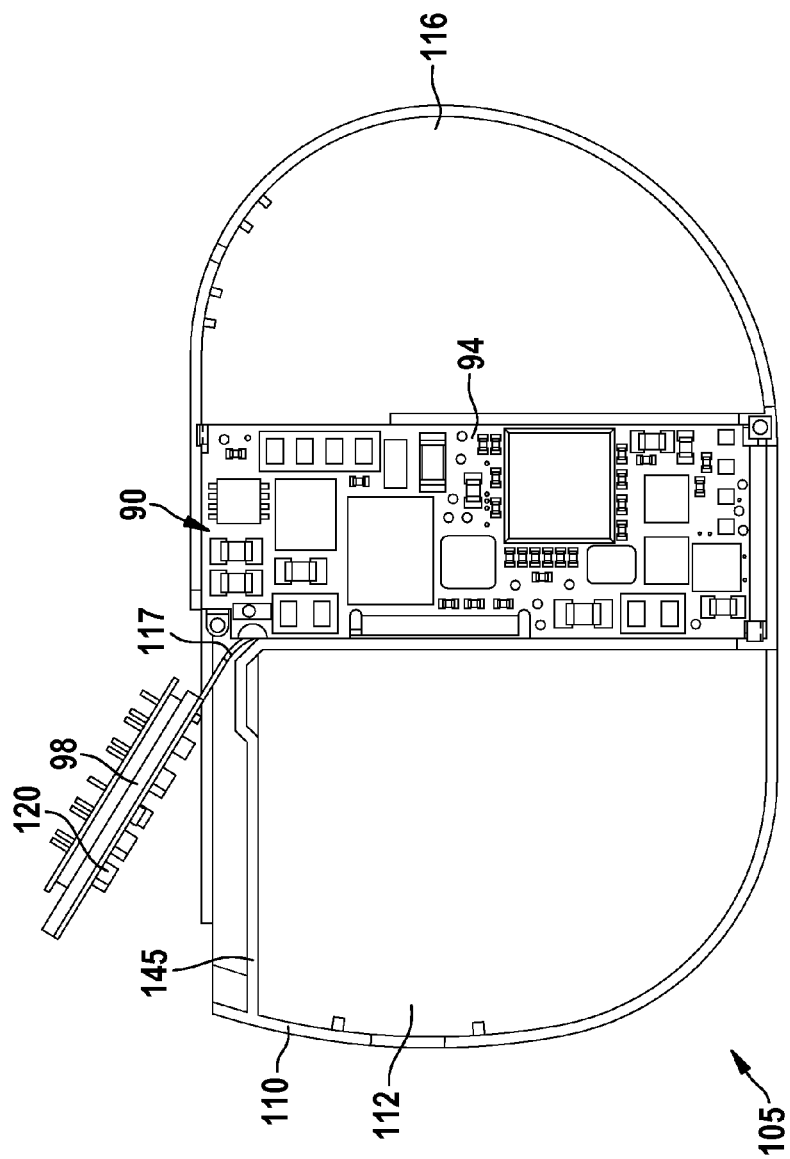
FIG. 4 is a side elevation view of the prior art device frame of FIG. 3, into which the flexible circuit board having a pre-folded extension shown in FIG. 3 has been mounted.

Referring to FIGS. 2-4, a package in the form of an electronic device housing 100 is shown (FIG. 2) that contains a closed, conventional internal frame 105 (FIGS. 3-4) for supporting electronic parts, such as, for example, the foldable flex circuit 90. Conventional frame 105 may be made of an electrically insulating material such as, for example, a polymer. Vertical members 107 and 108 of the frame 105 serve to compartmentalize space within the housing 100, which helps to prevent the electronic parts from shifting away from their factory-installed positions. In an exemplary preferred embodiment, the housing 100, into which the conventional frame 105 is designed to fit, takes the form of an implantable medical device (IMD) platform having a generally oval form factor, to which an outer perimeter 110 of the frame 105 conforms. In this example, the conventional frame 105 divides interior space within housing 100 into a left hand compartment 112, a center compartment 114, and a right hand compartment 116, enabling the IMD housing 100 to accommodate electronic parts of a compact cardiac therapy device, such as, for example, a pacemaker, implantable defibrillator, or a cardiac monitoring device, such as, for example, an implantable loop recorder. Such cardiac therapy devices may also accommodate, for example, a battery in the right hand compartment 116, and a telemetry unit in the left hand compartment 112. Connecting wires from the foldable flex circuit 90 then may be guided through a slot 117 located at an upper corner adjoining the center and left hand compartments 114 and 112, respectively, and then fed through an upper wall of the housing 100 to a header 118.

Referring to FIG. 3, electronic components 92 are shown mounted to both sides of the flexible substrate 94, which is shown partly folded. Upper extension 98 is shown at least partly pre-bent prior to inserting flexible substrate 94 into central compartment 114 of frame 105.

Referring to FIG. 4, the foldable flex circuit 90 is shown installed within central compartment 114 of conventional frame 105, with the extension 98 having been pre-bent so that it may be substantially aligned with an upper horizontal member 145 of outer perimeter 110.

Figure 5:
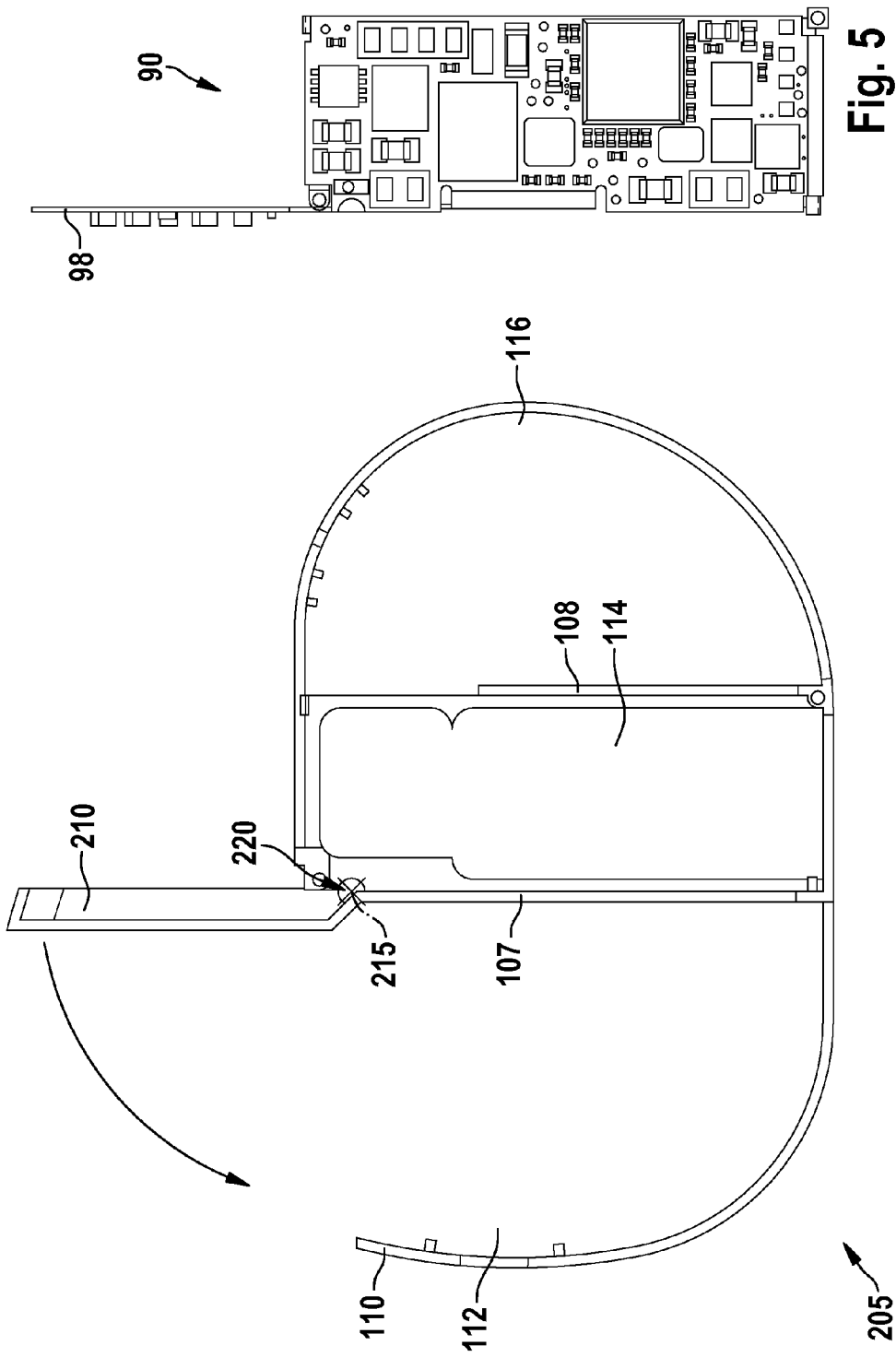
FIG. 5 is a side elevation view of a pivoting device frame and a flexible circuit board having an elongated extension.

Referring to FIG. 5, a novel fixture comprising a fold-assisting frame 205 is shown that accommodates the foldable flex circuit 90 without requiring a pre-bending operation. Designing and manufacturing one or more fold-assisting features as part of the frame 205 may be accomplished for a substantially similar cost as is currently incurred in designing and manufacturing the conventional frame 105. In addition, the novel fixture serves to eliminate equipment, accessories, fixation, and operator intervention associated with the pre-bending operation. More specifically, the fold-assisting frame 205 may take the form of a flexible, pivoting device frame such that in an exemplary embodiment, outer perimeter 110 of fold-assisting internal device frame 205 has, in place of the horizontal member 145 (see FIG. 4), a pivoting member 210 that pivots around a rotational axis 215, located at a pivot point 220. As one example of a fold-assisting feature, pivoting member 210 may be molded, recessed, or otherwise shaped to conform to contours of extension 98.

Figure 6:
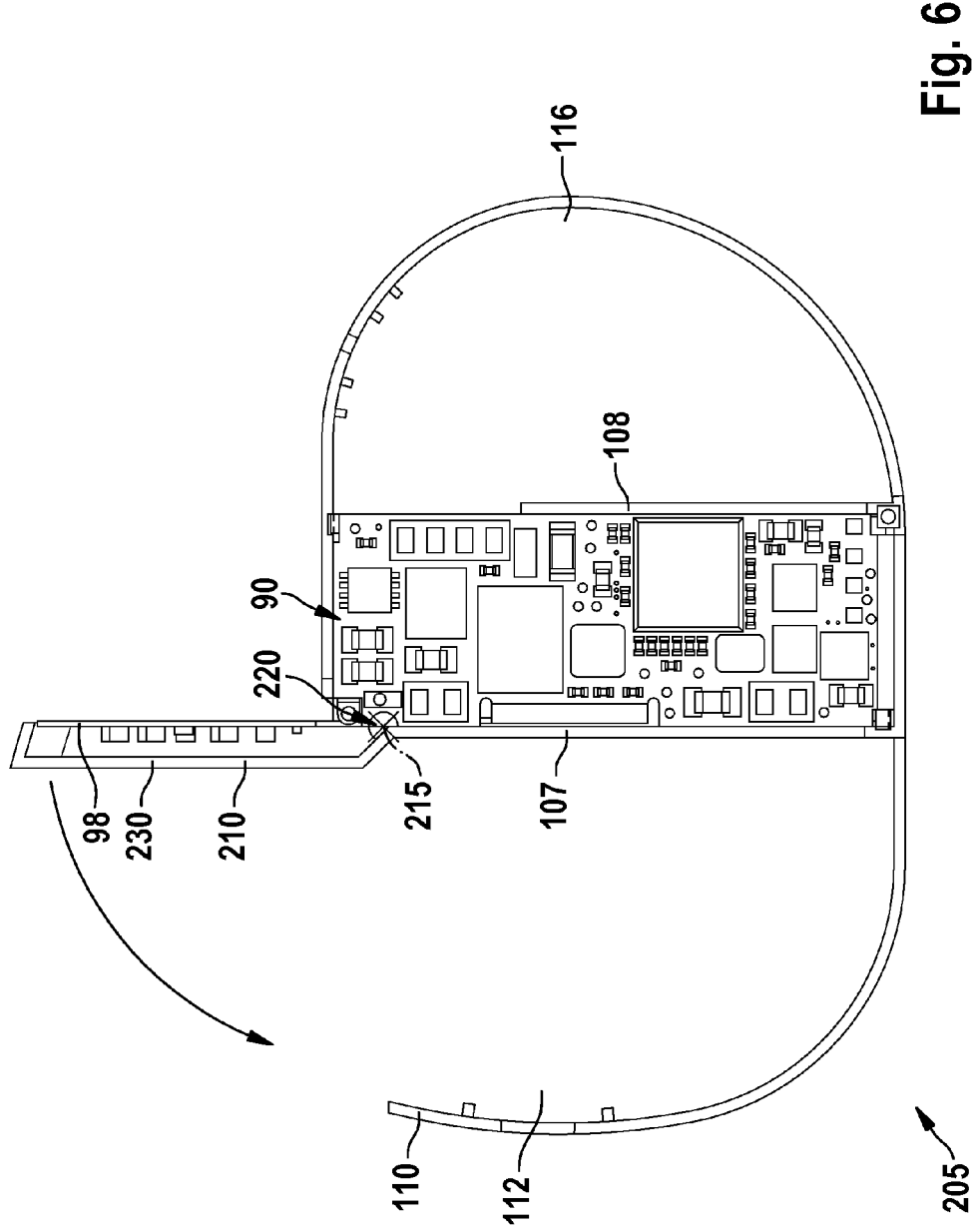
FIG. 6 is a side elevation view of the fold-assisting frame shown in FIG. 5 acting as a support structure to hold the flexible circuit board shown in FIG. 5.

Thus, as shown in FIG. 6, foldable flex circuit 90 may be placed into central compartment 114 so that upper extension 98 is in its upright position. Upper extension 98 may then be secured to pivoting member 210 by a retaining feature 230 in the form of, for example, a clip, a finger, or an edge clamp, that attaches to extension 98 without obstructing connections to components 92 mounted thereon.

Figure 7:
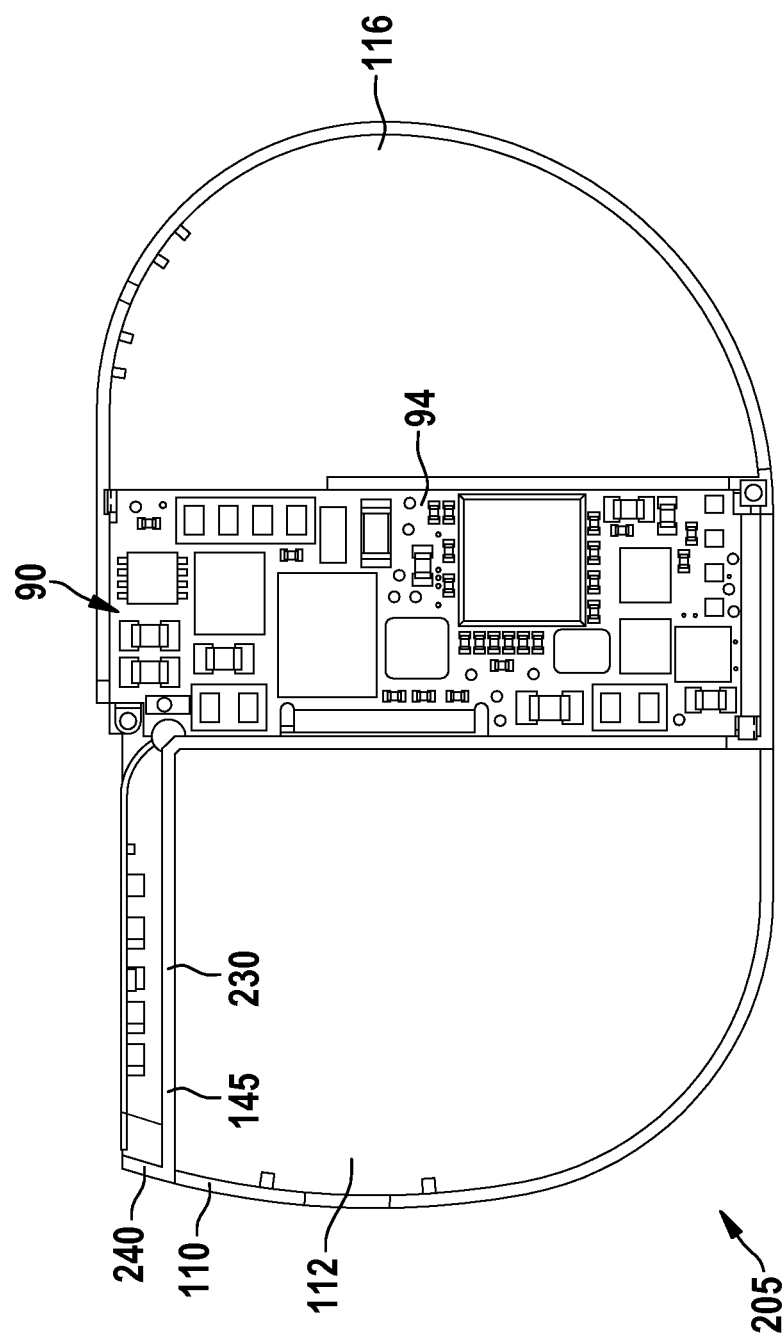
FIG. 7 is a side elevation view of the fold-assisting frame shown in FIGS. 5 and 6, supporting the flexible circuit board shown in FIG. 4, after completion of folding.

As pivoting member 210 is rotated 90-degrees counter-clockwise (as shown) around pivot point 220, extension 98 is thus folded into a desired three-dimensional configuration, as shown in FIG. 7. Upon completion of the folding step, a latching mechanism 240 may be provided to maintain the pivoting member 210 in its closed position. In the example shown, the final folded circuit configuration of extension 98 is such that connecting wires may emerge from the top surface of extension 98 to provide access for external connections to be made within header 118. In the case of an IMD, such external connections are made by feeding leads through openings in header 118 to mate with connecting wires on the top surface of extension 98.

In alternative embodiments, electronic parts may be associated with a different type of IMD, such as, for example, a neurostimulator, a different type of mobile electronic device, such as, for example, a mobile computing or telecommunications device, or even a non-electronic device, as long as all or a subset of device components 92 reside on a flexible substrate 94 that folds to fit within a package. A package, like housing 100, may therefore contain, in place of foldable flex circuit 90, an alternative arrangement of electronic, mechanical or micro-mechanical, chemical, or biological parts, or combinations thereof, mounted or otherwise attached to flexible substrate 94, and supported by a fixture comprising fold-assisting frame 205.

Figure 8:
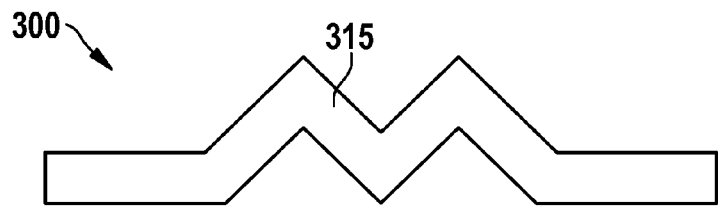
FIG. 8 is a diagram of a passive hinge for use in the fold-assisting frame shown in FIGS. 5-7.
Figure 9:
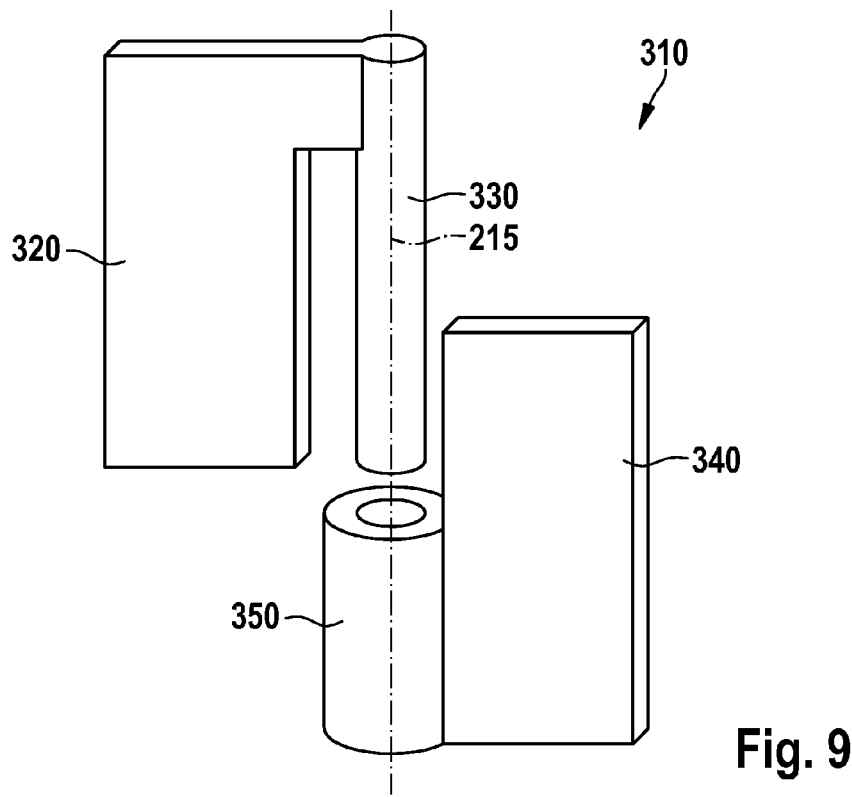
FIG. 9 is a side perspective view of an active hinge for use in the fold-assisting frame shown in FIGS. 5-7.
Figure 10:
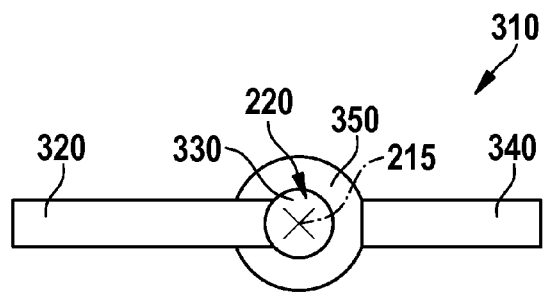
FIG. 10 is a top elevation view of the active hinge shown in FIG. 9.

With reference to FIGS. 8-10, shown are two alternative embodiments of a hinge that may be adapted for use in the fold-assisting device frame 205, and include a passive hinge 300 (FIG. 8) and an active hinge 310 (FIGS. 9 and 10), among other possible exemplary embodiments. Passive hinge 300 or active hinge 310 is preferably located at pivot point 220. Passive hinge 300 is embodied by a simple flexor 315 that facilitates bending the pivoting member 210. In FIG. 9, a side view of active hinge 310 shows how a first hinge flange 320 having a pivot post 330 may be joined to a second hinge flange 340 having a hollow cylinder 350. Pivot post 330 and hollow cylinder 350 are aligned along rotational axis 215, so that pivot post 330 may be inserted into hollow cylinder 350, enabling the first flange 320 to rotate about axis 215 with respect to the second flange 340, which remains in a substantially fixed position. FIG. 10 shows a top plan view of active hinge 310 thus assembled.

Although certain embodiments have been illustrated and described herein, it will be appreciated by those of ordinary skill in the art that a wide variety of alternative or equivalent embodiments or implementations, calculated to achieve the same purposes, may be substituted for the embodiments illustrated and described herein without departing from the scope of the present invention. Those of skill in the art will readily appreciate that embodiments in accordance with the present invention may be implemented in a very wide variety of ways. This application is intended to cover any and all adaptations and/or variations of the embodiments discussed herein.

The terms and expressions which have been employed in the foregoing specification are used therein as terms of description and not of limitation, and there is no intention, in the use of such terms and expressions, to exclude equivalents of the features shown and/or described or portions thereof, it being recognized that the scope of the invention is defined and limited only by the claims that follow.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. A method of folding a flexible circuit board, in situ, within a device frame, the method comprising the steps of:
   providing a flexible device frame of which at least a portion conforms to an interior shape of a device housing for implantation into a person's body, wherein the flexible device frame is a closed frame that includes an opening for receiving the flexible circuit board and a pivoting portion pivotal between an open and a closed position;
   inserting the flexible circuit board at least partially into the flexible device frame via the opening, wherein the flexible circuit board is inserted into the flexible device frame in a non-pre-bent condition, and wherein an upper extension portion of the flexible circuit board extends outside of the flexible device frame;
   with the pivoting portion in the open position and the flexible circuit board inserted in the flexible device frame, aligning the pivoting portion of the flexible device frame with the upper extension portion of the flexible circuit board;
   securing the pivoting portion to the upper extension portion of the flexible circuit board; and
   bending the pivoting portion of the flexible device frame to the closed position, wherein bending of the pivoting portion effectuates bending of the upper extension portion of the flexible circuit board together into a desired three-dimensional configuration to fit conformally within the device housing, wherein the bending step occurs while the flexible circuit board is received in the flexible device frame, and wherein in the desired three-dimensional configuration the pivoting portion of the flexible device frame is in the closed position,
   wherein the pivoting portion of the flexible device frame closes the opening in the flexible device frame such that the flexible circuit board is housed within the flexible device frame.

2. The method of claim 1, wherein inserting the flexible circuit board at least partially into the flexible device frame and aligning the pivoting portion of the flexible device frame to the upper extension portion of the flexible circuit board comprises placing the flexible circuit board into a central compartment of the flexible device frame.

3. The method of claim 1, wherein securing the pivoting portion to the upper extension portion of the flexible circuit board comprises securing the upper extension portion of the flexible circuit board to the pivoting portion by a retaining feature, wherein the retaining feature comprises a clip, a finger, or an edge clamp.

4. The method of claim 3, wherein the securing step is performed without obstructing connections to components mounted on the upper extension portion of the flexible circuit board.

5. The method of claim 1, wherein bending the pivoting portion comprises pivoting the pivoting portion around a rotational axis located at a pivot point.

6. The method of claim 5, wherein pivoting the pivoting portion comprises rotating the pivoting portion 90-degrees counter-clockwise around the pivot point.

7. The method of claim 1, further comprising the step of latching the pivoting portion of the flexible device frame to maintain the desired three-dimensional configuration.

* * * * *